United States Patent [19]

Tihon et al.

[11] Patent Number: 5,499,994
[45] Date of Patent: Mar. 19, 1996

[54] DILATION DEVICE FOR THE URETHRA

[75] Inventors: Claude Tihon; John H. Burton; Timothy C. Cook; David Rhum, all of New York, N.Y.

[73] Assignee: American Medical Systems, Inc., Minnetonka, Minn.

[21] Appl. No.: 234,196

[22] Filed: Apr. 28, 1994

Related U.S. Application Data

[63] Continuation-in-part of Ser. No. 99,892, Jul. 30, 1993, abandoned.

[51] Int. Cl.$^6$ .......................... A61M 29/00; A61M 5/00; A61F 2/04
[52] U.S. Cl. ....................... 606/192; 604/96; 604/104; 604/8; 604/54; 623/12
[58] Field of Search ........................... 604/93, 96–97, 604/104, 8, 264–265, 278, 54, 280, 286; 606/191–192, 194, 197–198; 623/1, 12

[56] References Cited

U.S. PATENT DOCUMENTS

| | | |
|---|---|---|
| 3,867,329 | 2/1975 | Halperrn et al. . |
| 4,026,296 | 5/1977 | Stoy et al. . |
| 4,237,893 | 12/1980 | Michaels . |
| 4,434,797 | 3/1984 | Silander . |
| 4,467,806 | 8/1984 | Bhiwandiwala et al. . |
| 4,480,642 | 11/1984 | Stoy et al. . |
| 4,611,584 | 9/1986 | Finney . |
| 4,655,771 | 4/1987 | Wallsten . |
| 4,732,152 | 3/1988 | Wallsten et al. . |
| 4,733,665 | 3/1988 | Palmaz . |
| 4,739,762 | 4/1988 | Palmaz . |
| 4,762,128 | 8/1988 | Rosenbluth . |
| 4,886,062 | 12/1989 | Wiktor . |
| 4,932,958 | 6/1990 | Reddy et al. . |
| 4,950,227 | 8/1990 | Savin et al. . |
| 4,955,859 | 9/1990 | Zilber . |
| 4,973,301 | 11/1990 | Nissenkorn . |
| 4,994,047 | 2/1991 | Walker et al. . |
| 5,059,169 | 10/1991 | Zilber . |
| 5,085,664 | 2/1992 | Bozzo . |
| 5,098,374 | 3/1992 | Othel-Jacobsen et al. . |
| 5,163,952 | 11/1992 | Froix . |
| 5,167,614 | 12/1992 | Tessmann et al. . |
| 5,192,289 | 3/1993 | Jessen . |
| 5,224,953 | 7/1993 | Morgentaler . |
| 5,234,456 | 8/1993 | Silvestrini . |
| 5,258,020 | 11/1993 | Froix . |
| 5,258,042 | 11/1993 | Mehta . |
| 5,269,802 | 12/1993 | Garber . |
| 5,282,860 | 2/1994 | Matsuno et al. . |

FOREIGN PATENT DOCUMENTS

| | | |
|---|---|---|
| 0467516A1 | 1/1992 | European Pat. Off. . |
| 576602 | 3/1993 | Japan . |
| 576603 | 3/1993 | Japan . |
| 2035350 | 6/1980 | United Kingdom . |
| 2139898 | 11/1984 | United Kingdom . |

Primary Examiner—C. Fred Rosenbaum
Assistant Examiner—Perry E. Van Over
Attorney, Agent, or Firm—Peter C. Richardson; Lawrence C. Akers; J. Trevor Lumb

[57] ABSTRACT

A device for dilating at least an obstructed portion of a urethra includes a hollow core member with opposed open ends permitting urination therethrough from the bladder, a confining covering disposed on the hollow member having a length of at least that of the obstructed portion and having hydrophilic means integrally associated therewith. The hydrophilic means is capable of absorbing water and gradually expanding for at least 30 minutes whereby the outer surface of the confining covering expands radially and outwardly, after insertion into the urethra, until dilation of the obstructed portion occurs to a desired diameter and configuration. Methods for dilating an obstructed portion of the urethra and for treating benign prostatic hyperplasia are also provided.

28 Claims, 7 Drawing Sheets

DILATION DEVICE FOR THE URETHRA

This application is a continuation-in-part of application Ser. No. 08/099,892 filed Jul. 30, 1993, and now abandoned.

BACKGROUND OF THE INVENTION

This invention relates generally to dilation devices for the urethra and to the treatment of hypertrophy of the prostate gland. More specifically it relates to novel devices for dilating obstructed portions of the urethra, and to concomitant methods for dilating an obstructed portion of the urethra and for treating benign prostate hyperplasia (BPH).

Benign prostate hyperplasia is a condition which affects well over 50% of the male population over 50 years of age. The treatment of BPH is a matter of great medical and commercial importance. On a worldwide basis, upwards of four billion dollars are spent annually in the treatment of this condition.

There are many devices, techniques and methods which are presently being employed for treating BPH. Surgical treatment of hypertrophy of the prostate has been a routine procedure for many years. One method of such surgical treatment is open prostatectomy wherein the gland is totally or partially removed. Another method of surgical treatment is transurethral resection of the prostate (TURP). However while surgical treatment can be effective it remains an extremely invasive procedure which is debilitating, painful and often traumatic to the patient. Various complications including impotence, incontinence, bleeding, infection and other undesirable problems attendant with such surgery can result. The need for less invasive procedures is therefore of considerable importance.

Among the less invasive procedures now being employed is that of using catheters which are placed in the external opening of the urethra and into at least the obstructed portions of the urethra which allow the passage of urine from the bladder by way of the catheter lumen. These urinary catheters typically employ a positioning or retention balloon at the distal tip which, at the bladder neck, when inflated, prevents the expulsion of the catheter from the body. Illustrative of such positioning balloon catheters are those known in the art as Foley catheters.

It has also been proposed to utilize inflation balloons in addition to positioning balloons for the purpose of dilating obstructed portions of the urethra. Illustrative of such type balloons are those described in U.S. Pat. No. 4,932,958 to Reddy.

It has also been proposed to utilize heat in combination with such catheters for treating the enlarged portion of the prostate, such heat being provided by a variety of means including the use of microwave or laser energy.

Again, while these methods and devices are useful, the search for even less invasive devices and procedures continues. The need for devices and procedures which will result in less pain and discomfort to the patient is of substantial interest, as is the desirability of providing means and devices which will provide for longer term patency of a dilated urethra, i.e. to effect a longer lasting result on relieving the obstruction in the urethra caused by the hypertrophied prostate gland. The latter, due to its resilient fibrous structure and large bulk tends to rebound after treatment of the obstructed urethra is completed, resulting in renewed obstruction.

It would be very desirable, therefore, to provide devices and methods for treating BPH which would be much less invasive and painful, and which would result in dilated urethras of longer patency.

Illustrative of a somewhat less invasive approach is found in the U.S. Pat. No. 4,762,128 to Rosenbluth. This patent discloses an expansion catheter having a rapidly expandable tubular stent associated therewith, which is adapted for transurethral insertion via the external opening of the urethra and for placement within an obstructed region of the urethral lumen caused by a hypertrophied prostate gland. Removal of the expansion catheter leaving in place an expanded tubular stent may result in long term patency of the urethral lumen. Though the stent is also adapted to be removable from the urethra, the intent of the device is to establish a long-term implant.

In U.S. Pat. No. 4,480,642 to Stoy et al, there is disclosed means for the slow dilation of the cervix utilizing a designated dehydrated hydrogel which upon swelling dilates the cervical channel.

In U.S. Pat. No. 4,467,806 to Bhiwandiwala et al, there is disclosed an osmotic cervical dilator using a sponge-like synthetic plastic body in which all the residual spaces are filled with a salt composition and the body is shaped for insertion and retention in the cervix, said dilator being slowly expandable.

In U.S. Pat. No. 3,867,329 to Halpern et al, there is disclosed a chemically actuated dilation device for insertion into the cervix or other body opening. The device to be inserted comprises a closed rod-like member composed of a hydrogel capable of expanding by the absorption of body or other fluids.

In U.S. Pat. No. 5,163,952 to Froix there is disclosed an expandable stent for use in a lumen defined by a wall of a vessel, which illustratively is defined as an arterial vessel in the heart. The polymeric stent has a built-in elastic predetermined diameter and a memory of a diameter greater than the predetermined diameter which is assumed upon activation of a thermal activation point by the adsorption of heat by the plastic, adsorption of liquid by the plastic, or a change in the pH of the liquid surrounding the plastic.

In U.S. Pat. No. 4,237,893 to Michaels there is disclosed a cervical dilator, sized, shaped and adapted to occlude the length of the cervical canal. The dilator comprises a base and a laminate formed of a swellable polymer.

In U.S. Pat. No. 4,434,797 to Silander there is disclosed a catheter for a body duct, vessel or cavity, which comprises an outer casing which entirely or partially covers the catheter and consists of a hydrophilic substance capable of absorbing liquid.

In U.S. Pat. No. 5,234,456 to Silvestrini there is disclosed a hydrophilic stent for a body lumen comprising a wall structure, at least a portion of which is hollow, which has a hydrophilic material disposed therein which can swell upon the introduction of a liquid.

SUMMARY OF THE INVENTION

In its broadest context, the present invention relates to a dilation device which can be inserted into at least an obstructed portion of a urethra, which comprises a hollow member with opposed open ends which will permit urination therethrough from the bladder, the member having a length between said opposed ends of at least that of the obstructed portion and having hydrophilic means integrally associated therewith which is capable of absorbing water. The hydrophilic means is of the kind capable of gradually swelling after insertion into the urethra to effect dilation of the obstructed portion of the urethra to a desired diameter and configuration. The hollow member or core will usually be rigid and non-expandable, although under certain circumstances it may also be expandable.

Also in its broadest context, the present invention provides a method for dilating an obstructed portion of a urethra such as would occur from the hypertrophy of the prostate gland, which method comprises the steps of inserting a device into the urethra, the device comprising a hollow member or core, having a lumen therewithin and having opposed open ends which will permit urination therethrough from the bladder, the device also having hydrophilic means integrally associated therewith which are contained within an expandable confining covering, the hydrophilic means being of the type adapted to swell gradually when water is absorbed by said means; disposing the device within at least the length of the obstructed portion; leaving the device within the obstructed portion of the urethra until the hydrophilic means swell to a predetermined extent thereby to cause the confining covering to expand radially outwardly; continuing the radial expansion until dilation of the obstructed portion occurs to a desired diameter and configuration; and thereafter removing the device from the urethra.

The present invention also provides a method for treating benign prostatic hyperplasia which comprises the aforesaid method of dilating an obstructed portion of the urethra thereby relieving the obstruction caused by the hypertrophy of the prostate gland.

In accordance with this invention, the hydrophilic means for expanding radially outwardly within the urethra are of the type which will absorb water and will gradually expand for a period on the order of at least about 30 minutes and preferably much longer. In the latter regard, an expansion at a rate of about 6 French to about 10 French over a 24 hour period is desirable to effect the dilation of at least the obstructed portion of the urethra to a maximum or desired diameter and configuration. This gradual dilation has the significant advantage of alleviating or lessening the discomfort felt by the patient which is the concomitant effect when fast, virtually instantaneous dilation of the urethra occurs, as is the case with dilation means currently employed in dilating the urethra, as for example with balloon catheters or balloon actuated expansion devices. It is an important attribute of this invention that the hydrophilic means will swell and expand outwardly and radially in situ, i.e. within the confining covering, such as due to the uptake of body fluids. Most usually in the context of this invention the hydrophilic means will be activated due to the absorption of water from urine coursing from the bladder.

The "gradually" expanding hydrophilic means can be any biologically compatible materials such as hydrogels which are capable of expanding slowly when water is absorbed therewithin. Among the hydrogels which are employable in the context of this invention are those utilized heretofore in cervical dilators, or in cervical devices such as described in U.S. Pat. No. 3,867,329. Known slowly expanding dilators such as laminaria digitata or japonica can also be utilized.

Another aspect of this invention is the fact that the devices of this invention can be adapted to remain in the urethra for extended periods of time before removal. Such an extended presence can be on the order of at least about 5 days to about 30 days, the latter being a desirable upper limit because of clinical efficacy and patient comfort. As a consequence of the long presence of the expanded device in the urethra, the dilated urethral configuration will tend to remain in such configuration for an extended period of time, even after the device is removed. Up to 12–24 months or more is likely before obstruction of the prostatic urethra will occur again. This is a highly desirable result of this aspect of the invention. As stated above, in the prior means employed for rapidly dilating obstructed portions of the urethra, deformation of the urethral wall will often have a relatively short effect on relieving the obstruction of the prostatic urethra because the latter is caused by the continued pressure exerted by the hypertrophied prostate gland, due to the resilient viscoelastic nature of its tissue.

While in the context of this invention it is important that means for removing the devices of this invention be provided, the type of such means is not narrowly critical. For example, pull string configurations and mechanical emulsification and aspiration means can be employed.

It is also important that the devices of this invention be adapted to remain in the urethra in their expanded form without moving spontaneously from their intended position or without being unintentionally expelled from the urethra by urination or other bodily movement or activity. Accordingly, the devices of this invention can be provided with fixing or anchoring means such as described hereinafter which will enable the devices to remain in the dilated portion of the urethra for the desired time without slippage or spontaneous movement out of the urethra or up into the bladder.

In accordance with the specific aspect of this invention, a dilation device or stent for opening a portion of a urethra obstructed as for instance as a consequence of a hypertropied prostate gland includes an inner member or core which defines a lumen therewithin having opposed open ends, the lumen being a conduit of sufficient diameter to permit urine to flow freely therethrough from the bladder. At least a portion of the device also includes an outer confining covering deployed about the inner member or core, which covering is capable of expanding radially outwardly to a predetermined, preferably self-limiting, extent. The covering is further adapted to be placed contiguously with the obstructed portion of the urethra and is of a length at least partially that of such obstructed portion.

The gradually expanding hydrophilic material of the kind indicated above, are contained within the covering which as described hereinafter is preferably in the form of an envelope having an outer surface capable of distending to a predetermined extent, e.g. 70 French, or in another preferred embodiment, in the form of a collapsible and expandable bag which has an elastic outer surface capable of extending to the extent where equilibrium is attained between the radial pressures of the slowly expanding hydrophilic material and the pressures exerted by the prostatic tissue. The inner member or core is non-collapsible under the pressure that would emanate from the hypertropied prostate gland and also from the internal pressures exerted by the effect of the swelling of the hydrophilic material. The inner core also contains access means, e.g., orifices, of a diameter sufficient to enable body fluids to pass through the core or member in a radially outwardly direction, thereby to interact with the hydrophilic material to cause the latter to swell, the outer covering thereby expanding radially outwardly to impact upon the prostate gland, until dilation of the obstructed portion of the urethra occurs to a desired diameter and configuration. It is important that the diameter or cross-sections of the orifices be less than the diameter or cross-sections of any hydrophilic material, even in their non-swollen state, to prevent such material from passing back into the lumen. The flow of body fluids, therefore, in the context of this invention, is normally unidirectional.

Further objects, features and advantages of the present invention will become apparent from the detailed description of the drawings.

DETAILED DESCRIPTION OF THE DRAWINGS

Figure 1:
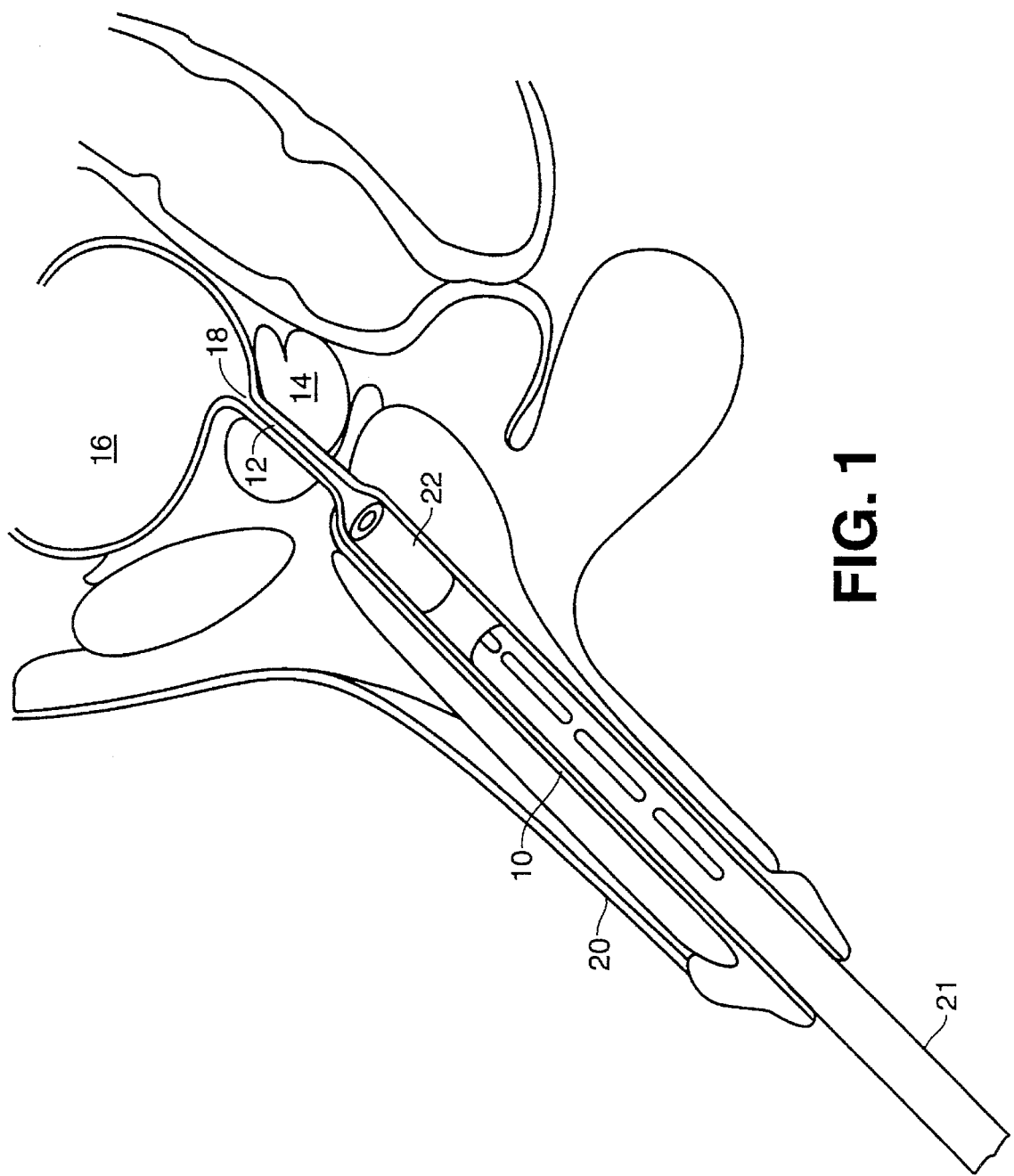
FIG. 1 is a simplified sectional view of the relevant anatomy of a male body, showing an obstructed urethra, an enlarged prostate gland, a bladder, a schematic delivery tool and an unexpanded dilation device of the subject invention, as hereinafter described, which is positioned just before insertion into the obstructed portion of the prostatic urethra.

In the drawings like reference numerals are utilized for like parts throughout the several views. In FIG. 1 there is illustrated in simplified form, a urethra 10 having an obstructed portion 12 about which is depicted an enlarged hypertrophied prostate gland 14, which inferentially is pressing inwardly on the obstructed portion 12. Also shown is a bladder 16 having a neck 18 depending therefrom, and at the other end of the urethra is a penis 20. A dilation device 22 according to the subject invention, which will be hereinafter described, is shown in position to be inserted into the urethra, the device being of a length at least equal to that of the obstructed portion 12. A simulated tool 21 is also shown for delivering the device 22.

Figure 2:
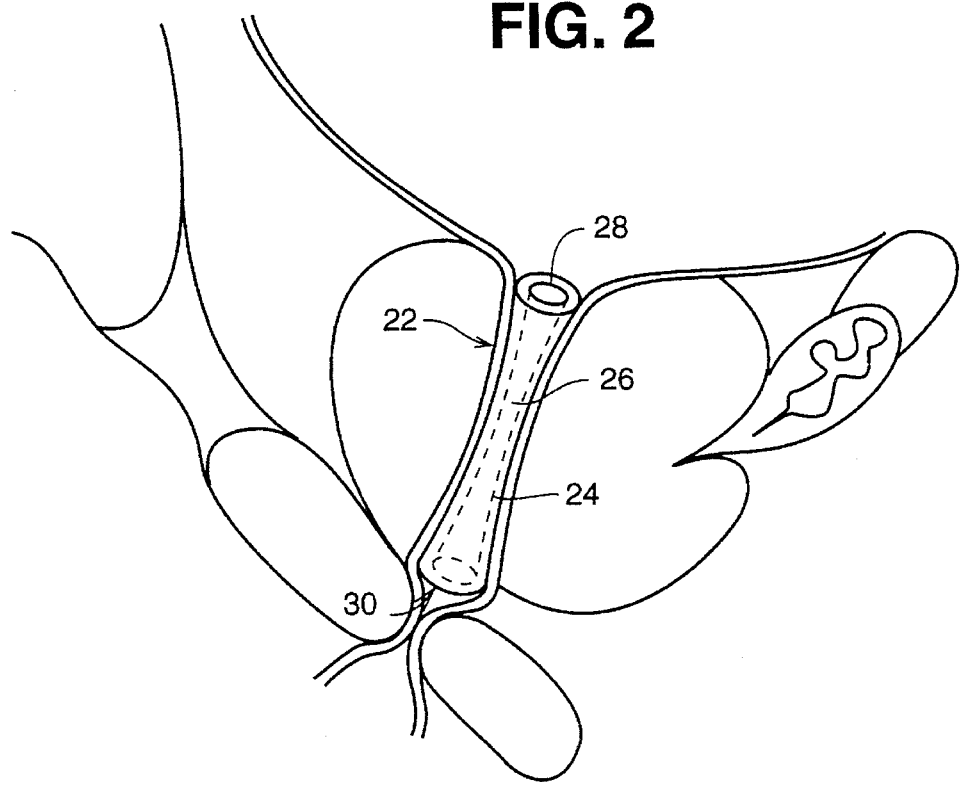
FIG. 2 is a sectional view of a portion of FIG. 1 depicting a dilation device of the subject invention in a non-expanded state implanted within the obstructed portion of the urethra.

In its broadest context the device 22, as shown in FIG. 2, comprises a hollow member (a core or tube 24) which defines a lumen 26 therewithin having open ends 28 and 30 which permit urine to flow from the bladder through the urethra and out of the penis. The lumen acts as a conduit having a diameter sufficient to permit urine to freely flow therethrough.

Figure 3:
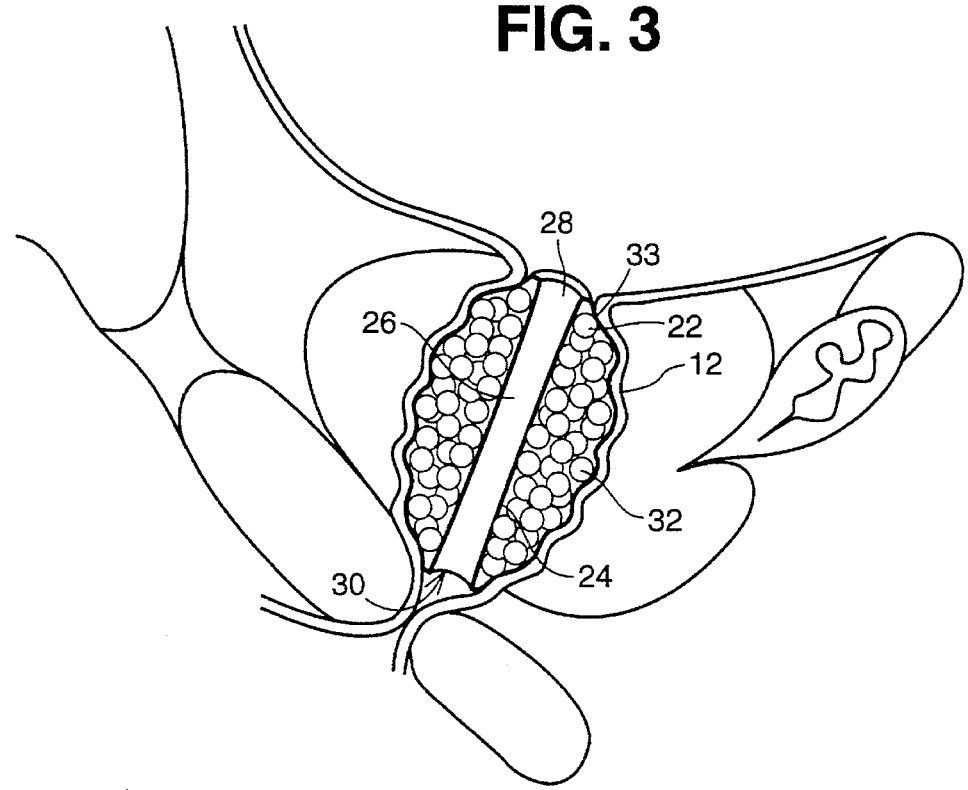
FIG. 3 is a perspective view of a dilation device of the subject invention implanted within the obstructed portion of the urethra, in an expanded state, and indicating the concomitant dilation of the prostatic urethra.

Again, in its broadest context, the device 22 includes for at least the length of the obstructed portion, hydrophilic means 32, shown in FIG. 3, which are defined within confining covering 33. The means 32 are of the type capable of absorbing water and gradually and slowly swelling and expanding for at least 30 minutes and preferably much longer. Confining covering 33 comprises a material capable of expanding outwardly and radially. As a consequence of the swelling of the hydrophilic means the covering 33 expands outwardly and radially with sufficient force to impact upon the hypertrophied prostate gland, thereby expanding and dilating the obstructed portion of the urethra 12 to a predetermined diameter and (dilated) configuration. In FIGS. 1 and 2 the hydrophilic means would be in its unexpanded state, i.e. it has not yet absorbed water such as would emanate from the passage of urine through the lumen 26.

The device 22 in its unexpanded state should be of a minimum diameter, including the hydrophilic means-containing portion, that would allow the device to be inserted into the penis and then into the obstructed portion of the urethra with a minimum of discomfort. A suitable minimum diameter in this regard should be about 20 to about 26 French. (1 French=⅓ mm).

In FIG. 3, the section or portion of the device 22 having hydrophilic means 32 is depicted in an expanded, inflated state, and the portion 12 of the urethra, formerly obstructed by the hyperplasia of the prostate gland, is now shown in a dilated configuration.

Figure 4:
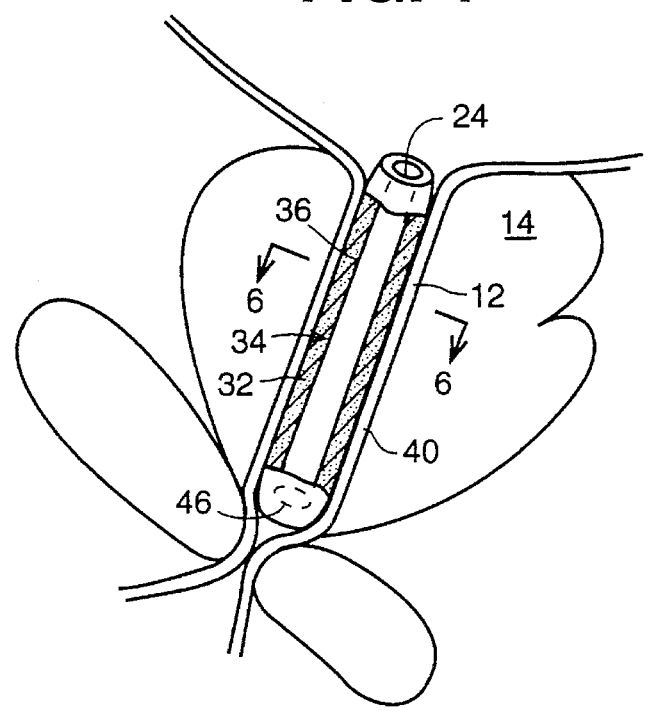
FIG. 4 is a perspective view of the envelope embodiment of this invention in an unexpanded state.
Figure 5:
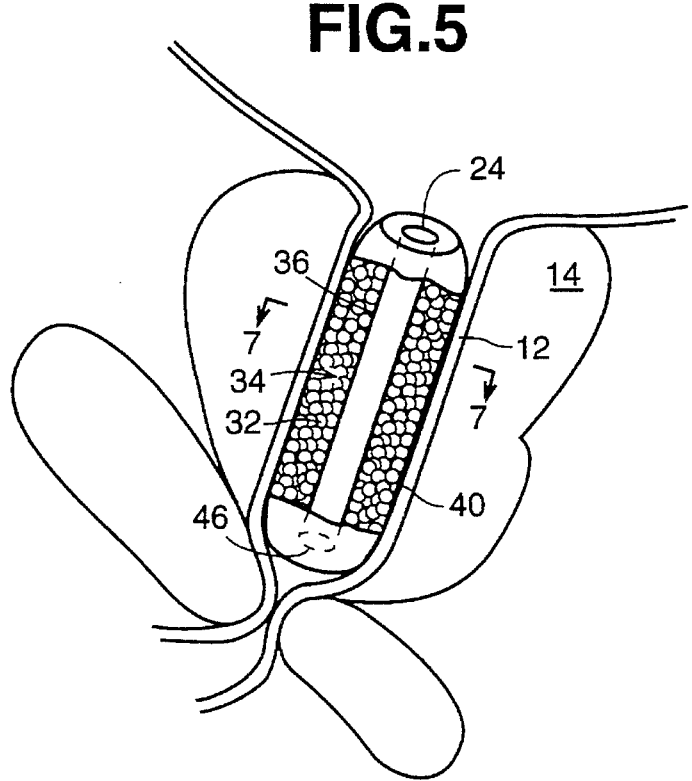
FIG. 5 is a perspective view of the device of FIG. 4 in an expanded state, and indicating the concomitant dilation of the prostatic urethra.

A preferred embodiment of the subject invention is shown in FIGS. 4 and 5. In FIG. 4 a non-expanded envelope 34 is disposed about the hollow member 24, and is attached to the hollow member or core 24 adjacent to the bladder neck and the bulbous urethra. It is also possible to have the envelope with both inner and outer surfaces in a form of a "glove" about a hollow member (or core) 24, the envelope being contiguous with the obstructed portion 12 of the urethra. Within the envelope 34 are the hydrophilic means 32 referred to above, (shown more clearly in FIG. 5) such as in the form of hydrogel particles which are capable of absorbing water and gradually and slowly expanding when so absorbing water, such as would emanate from urine flowing from the bladder.

Figure 6:
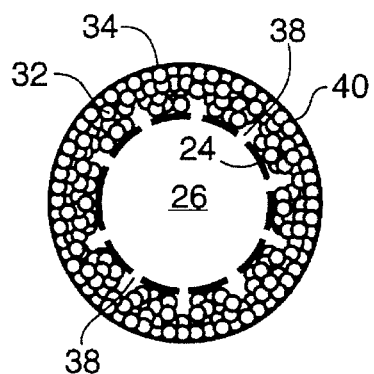
FIG. 6 is a transverse cross-sectional view of the device of FIG. 4 through the axis 2—2.
Figure 7:
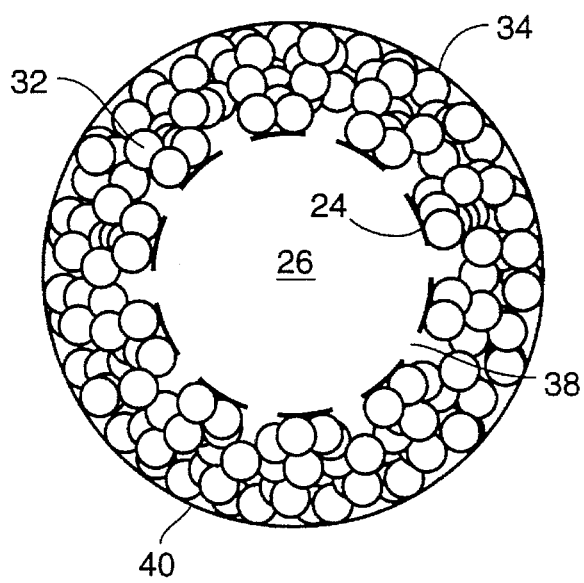
FIG. 7 is a transverse cross-sectional view of the device of FIG. 5 through the axis 2—2.

The inner surface of the core 24 in this embodiment contains perforations or pores 38, shown in FIGS. 6 and 7, shown in exaggerated dimensions, which permit the easy influx of fluid, i.e. urine, into the non-expanded confines of the envelope and the hydrogel particles. When the urine comes into contact with the hydrogel particles the latter commence to swell, slowly and gradually, thereby causing the outer surface 40 of the envelope 34 to expand outwardly and radially, thus causing a continuous and eventually forceful impact upon the hypertrophied prostate gland. As a consequence the latter is forced to recede.

To insure the expansion radially and outwardly the core 24 (containing the aforesaid perforations or ducts) is typically composed of a non-collapsible and inwardly non-distensible material. On the other hand, the outer surface 40 of the envelope 34 is composed of material capable of distending under the aforesaid desired outwardly and radially-applied pressure and force to the extent which is predetermined.

As stated heretofore, the diameter of the unexpanded devices of this invention should be on the order of between about 20 and about 26 French. Generally speaking, diameters of less than about 20 French will not permit adequate urination in combination with desired dilation, while the insertion into the meatus of the penis prior to insertion into an obstructed prostatic urethra of an unexpanded device having a diameter of more than about 26 French will usually be too painful for a patient. It thus follows that the minimum diameter of the lumens of the devices of this invention should be fixed within the tolerable limits of the diametral range of the unexpanded device, preferably on or about 20 French. However, within this range the lumen diameter can vary depending on the hydrophilicity of the expandable particles.

FIG. 5 depicts an expanded envelope 34. As shown, the hydrogel particles, i.e. the hydrophilic means 32, are now in an expanded mode, which has distended the outer surface 40 outwardly and radially. The affinity of the hydrogel particles for water plus the distensibility and non-distensibility of the outer and inner surface respectively of the envelope keep the direction of expansion in the desired mode.

The outer surface 40 of the envelope 34 can also self-limit the expansion by the nature of the material employed for such surface. For example the degree of elasticity of the outer surface 40 should permit expansion on the order of 100–1000% of its initial dimension, with a diameter of about 45–70 French being suitable. The hydrogel particles also should have a limit to their expansion, which can usually be arrived at when equilibrium is reached, i.e. when such particles are saturated by water. This is a self-limiting characteristic of many of the materials useful in this invention.

The extent of dilation is usually self-limiting based upon a number of chemical or mechanical properties. For a chemical effect the ion or solute within solution will cause expansion to a point where equilibrium or equilibration of this ion is reached within and around the stent. From a mechanical aspect if one were to use an envelope which had been pre-oriented for only 60 French, no matter how much hydrophilic material was placed within this envelope it would only expand to 60 French, even though the osmotic concentration may not have reached an equilibrium. A second mechanical limitation may be the inward radial force on the stent itself from the prostate. The prostate has smooth muscle which will have a basal tone. This is distensible only to a certain point.

The non-collapsible, inner core 24 may be fabricated from any number of known biocompatible materials such as polyethylene, polycarbonate, and polysulfone. The outer surface of the envelope 34, which has to be distensible to a predetermined extent, may also be fabricated from suitable biocompatible materials such as polyethylene, polyester terethalate (PET) and high modulus polystyrene.

As stated above, in the context of this invention, the hydrophilic particles must be capable of gradually (as opposed to rapidly) expanding. This provides a maximum of comfort to the patient whereas rapid swelling and expansion can be painful for the patient. Further, a slow rate of expansion provides for a longer patency for the dilated urethra even after the device 22 is removed from the urethra. Among the hydrophilic materials useful in the practice of this invention are polyvinylpyrrolidone, polyethylene glycol, karaya gum, carboxy methyl cellulose, hyaluronic acid, dextran, polyacrylic acid, polyvinyl alcohol and other organic polymers containing carboxylic acid groups or their salts. Cross-linked hydrophilic polymers or hydrogels are particularly desirable. These should be insoluble yet still capable of expanding up to 1000% due to the absorption of water. Cross-linking may be by chemical means or by physical means. The hydrogels disclosed in U.S. Pat. Nos. 3,867,329 and 4,480,642 can also be useful in this invention. Reference can also be made to G.B. 2,139,989A for suitable cross-linked polymeric compositions.

The concentration of hydrophilic material will also affect the rate of expansion. A high concentration of such material will speed the rate of expansion. Also a high osmolarity, or charge content, will speed the rate of swelling. A particularly advantageous range of slow expansion for the stents of this invention, will be at the rate of about 6 French (or less) to about 10 French, over a 24 hour period.

In FIGS. 6 and 7 a cross-section of the device of FIGS. 4 and 5 through the axis 2—2 is shown. In FIG. 6, the non-expanded device of FIG. 4 is shown on an enlarged scale wherein non-expanded hydrogel particles 32 are disposed in tightly clustered relationship in the envelope 34 between the non-collapsible inner core 24 and distensible outer surface 40. The envelope 34 is shown annularly positioned about the core 24 which defines the lumen 26. Placed throughout core 24 are perforations or orifices 38 which permit the easy access of urine into the hydrogel packed within the envelope 34. It can be appreciated that in the obstructed condition, the lumen in fluid communication with the bladder will have a narrow diameter less than the aforementioned diameter necessary for the device to be implanted.

In FIG. 7, on an exaggerated scale, the expanded envelope of FIG. 5 is shown through the aforesaid section 2—2. Hydrogel particles 32 have swelled due to the absorption of water from the urine resulting in an outward, radial expansion, thereby effecting the dilation of the urethra to a desired but usually self-limited diameter and configuration.

The gradual, slow dilation of the hydrophilic means should occur over a period of at least 30 minutes, and preferably over a much longer period, a dilation which occurs at a rate of about 6 French per 24 hour period being particularly desirable. Thus if a dilated stent of 70 French is desired, and the initial stent diameter was about 20 French, the slow dilation could take as long as 7 or 8 days. A long expansion or swelling period may also be helpful in a longer patency for the resulting dilation. In this regard, the device of the subject invention is adapted to remain in the urethra for periods on the order of seven days to 30 days, the latter being a practical upper limit for retention in the urethra for biocompatible reasons, such as possible urinary tract infection, increased inflammation or bacterially based prostatitis.

Figure 8:
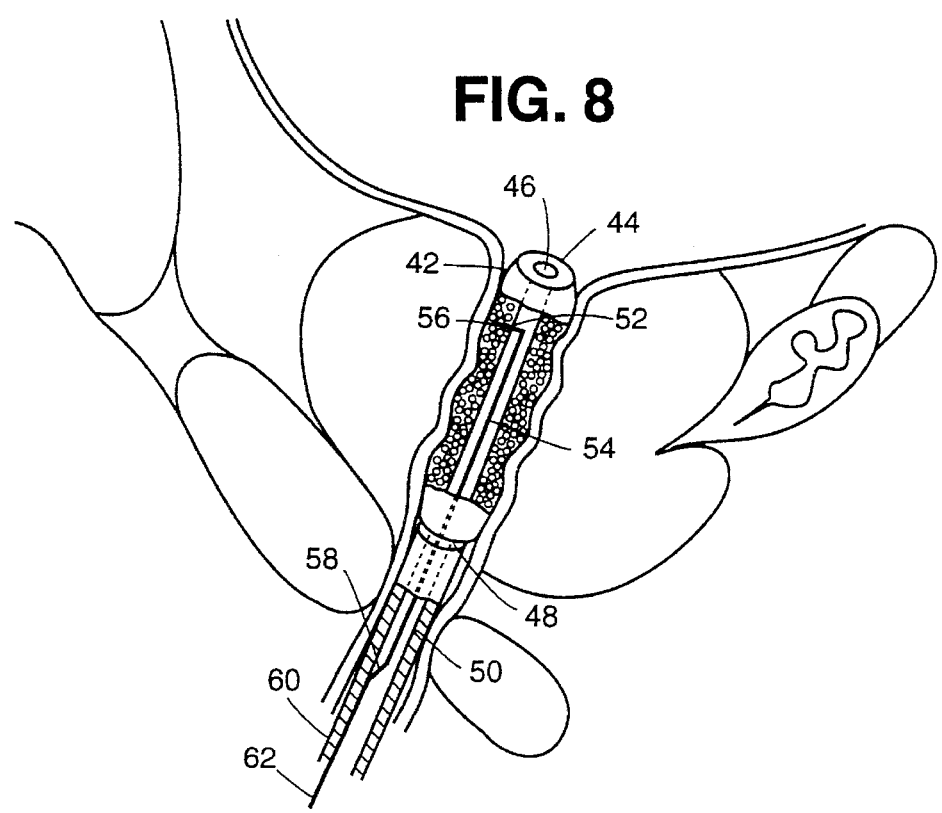
FIG. 8 is a perspective view of the collapsible bag embodiment of this invention in an unexpanded state.
Figure 9:
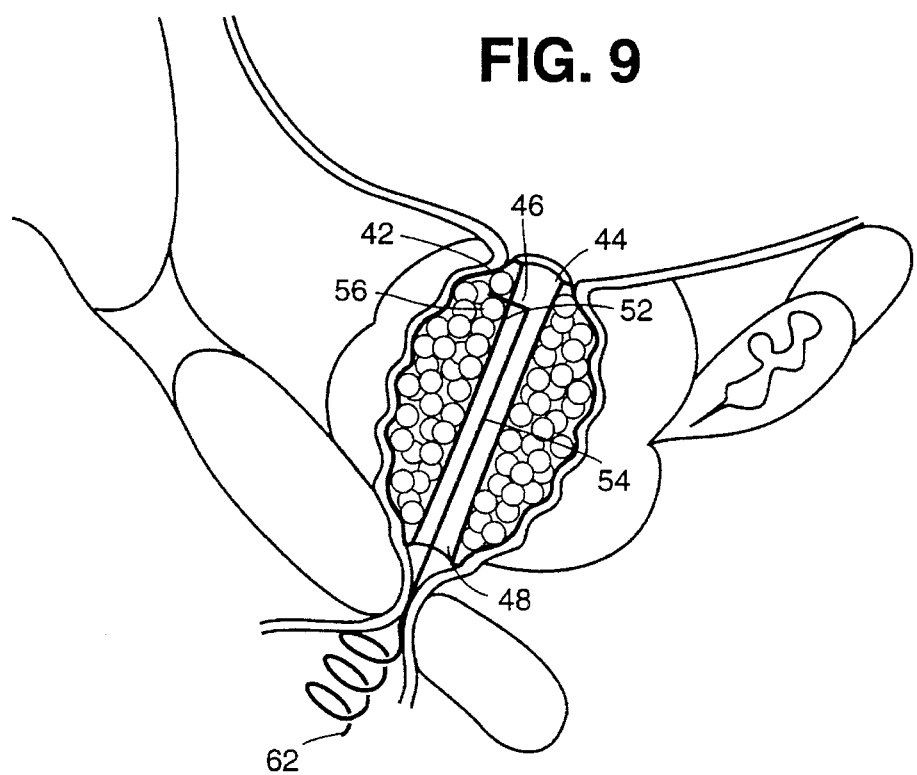
FIG. 9 is a perspective view of the embodiment of FIG. 8 in an expanded state, with anchoring means affixed thereto.

Another embodiment of the subject invention is represented in FIGS. 8 and 9. In these figures there is shown a slowly expanding bag stent 42. FIG. 8 depicts the bag in a collapsed state containing an unexpanded hydrophilic particles which are capable of swelling over the passage of at least 30 minutes and preferably over more than 48 hours. The bag is constructed around an open-ended hollow tube or core 44 which defines a lumen 46, the latter having a diameter which allows the free flow of urine therethrough, emanating from the bladder. Small orifices or perforations (not shown) such as described in the envelope embodiment, are present in the hollow tube or core, which permit the flow of urine into the bag and into contact with the gradually expandable hydrophilic particles. End 48 of the tube has means, for attachment to a placement tube 50, the latter being capable of being disconnected on command. Attached to tube 44 at point 52 is wire or filament 54. As shown in FIG. 8 (and FIG. 9) the wire or filament 54 is attached by a hook 56 which passes through the tube or core 44.

Figure 12:
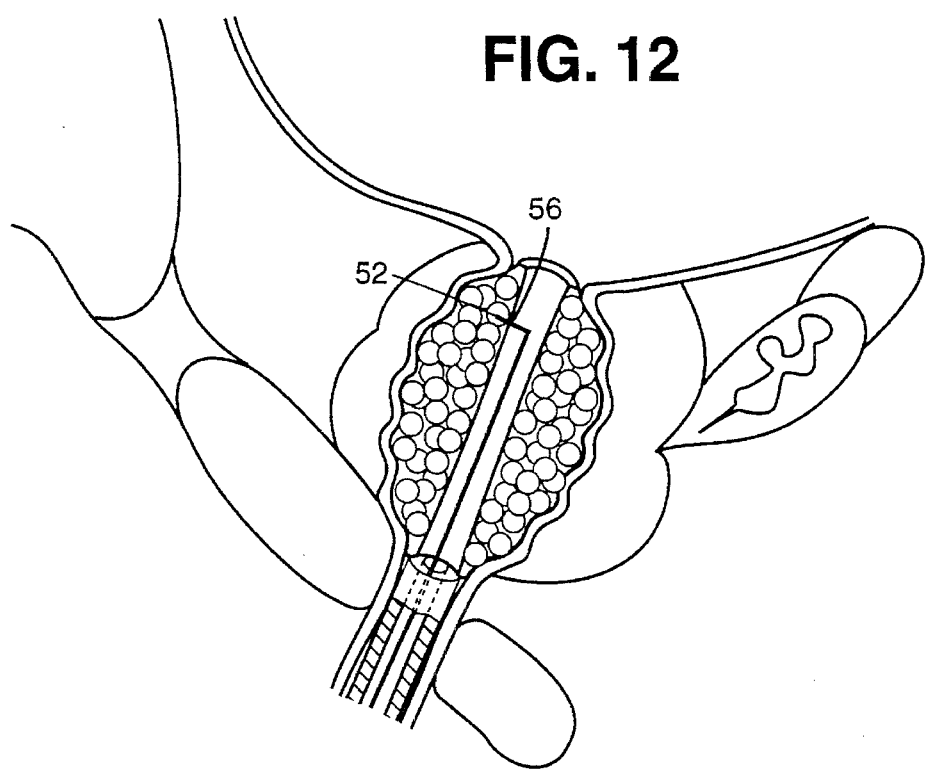
FIG. 12 is a perspective view of the embodiment of FIG. 9 indicating the inception of removal of the device.
Figure 13:
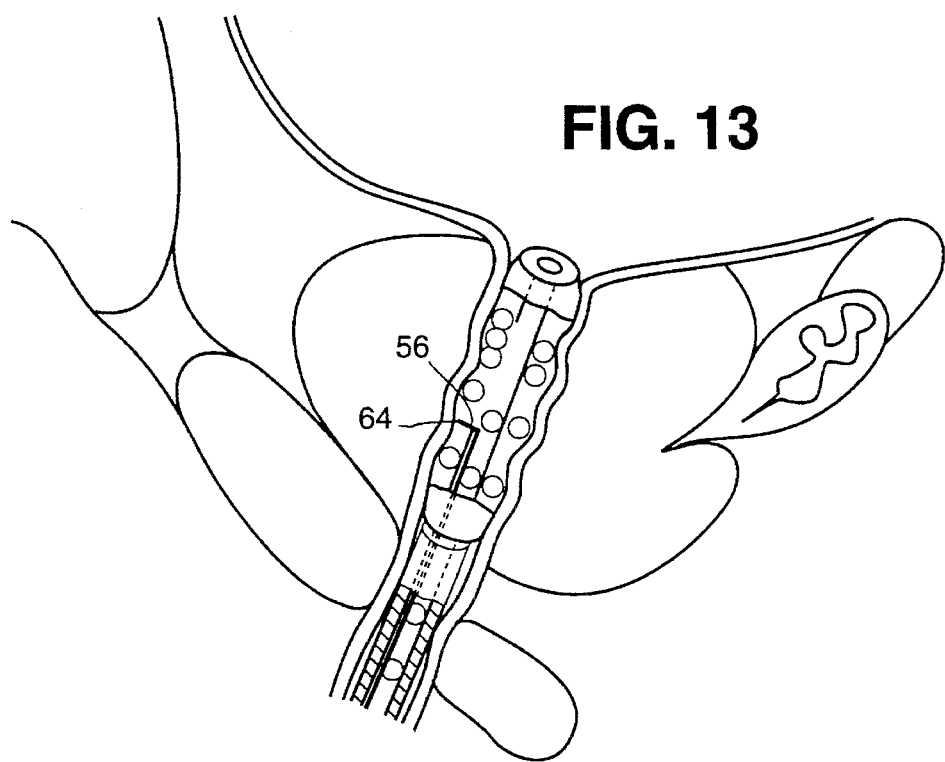
FIG. 13 is a perspective view of the embodiment of FIG. 12 showing the feature of tearing the bag to permit removal.

As shown in FIG. 8 the wire or filament exits from the tube 44 through opening 48 which when placed in the body is proximal to the external sphincter. Wire or filament 54 contains a portion 58 which has a coiling propensity when not under restraint. However, when restraint is removed, the portion 58 of the wire will coil as shown in FIG. 9. When the device of the embodiment is ready for insertion into the urethra a detachable sheath 60 is disposed as shown. Sheath 60 constrains the wire such that portion 58 is in its narrowed, i.e., straight, mode. When sheath 60 is removed the portion 58 assumes a coiled state or mode as shown in FIG. 9. To remove the device from the urethra a pulling force can be applied to end 62 of wire 54. This causes the coil to again straighten. When a further downward force is applied hook 56 moves from the point 52 to point 64 which is shown in FIG. 13. The sequence is shown in FIGS. 12 and 13. This movement of the hook creates a large longitudinal opening or tear in the core and the bag. The swelled particles then may flow freely from the bag into the lumen of tube, thus collapsing the bag, also as shown in FIG. 13. The collapsed bag, with remaining particles; can thus be easily removed, e.g., by aspiration.

In this embodiment, the collapsed bag device is introduced transurethrally, such that the bag is in the prostatic urethra and coilable portion 58 of the wire 54 is in the region of the external sphincter. The bag embodiment of this invention differs from the envelope in that the outer surface of the latter is expandable to a predetermined extent, while the outer surface of the bag, which is elastic, will extend to the extent where there is equilibrium between the radial pressures exerted by the slowly expanding hydrophilic material and the pressures exerted by the prostatic tissue.

One of the advantages of the bag embodiment of this invention is that it enables a greater amount of hydrophilic material to be employed. In this regard, an initial diameter of about 20 French is the most comfortable size of a device to be inserted through the penis into the urethra. This means that only about 1 gm of hydrophilic material can be inserted initially into the envelope or collapsed bag embodiments. In a fully expanded state this would provide a dilation of about 60 French. With the bag embodiment, however, additional hydrophilic material can be further provided after insertion, thus permitting greater outward radial expansion, on a order of 75 or even 90 French. With slow dilation this does not become appreciably uncomfortable for the patient.

The dilation devices of this invention can also be modified in various other ways. For example, while the inner surface of the core member can be made of a non-distensible material containing perforations and orifices, this member can also be composed of a water permeable or porous membrane or laminaria material which will not distend but will still allow easy access for urine to pass into contact with the hydrophilic material, by osmosis. It is important, however, that the access means be unidirectional, i.e. that the perforations etc. are of a diameter which permit urine to flow into and be absorbed by the hydrophilic material, but not permit the backflow of hydrophilic material or particles into the urethral canal.

Further, as will be seen when discussing anchoring means, the outer distensible surface could itself contain perforations for permitting some expanded hydrogel material to be emitted in advance of the outer distensible surface.

As stated previously, the dilation device of this invention is adapted to be removed after the passage of an extended period, on the order of from about 5 to about 30 days. The means for removal of the device is not narrowly critical and means now available can be used for that purpose. For example, mechanical means, emulsifying means, ultrasound cavitation, can be employed.

It would also be possible to attach a pull string to the open end of the device nearest the penis, which could be utilized to effect removal of the device. Removal could also be effected by aspiration, i.e. the dilation device could be removed by suction. It would also be possible to employ materials for the device, and to employ hydrogels or other hydrophilic means, which would dissolve by the action of body fluids or enzymes after the passage of an extended period of time and pass out of the body as part of material excretion. It is also contemplated that a tool capable of puncturing the swollen envelope embodiment of .this invention could also be employed.

While the manner of removal of the device is not narrowly critical, it is important that slippage or movement of the device, particularly of that portion contiguous with the obstructed portion of the urethra, be prevented or greatly minimized. In this regard slippage or movement can occur not only out of the urethra in the direction of the penis, but upwards into the bladder. Accordingly, this invention also contemplates the use of an anchoring or fixing means to keep the dilation device in place for an extended period of time.

Figure 10:
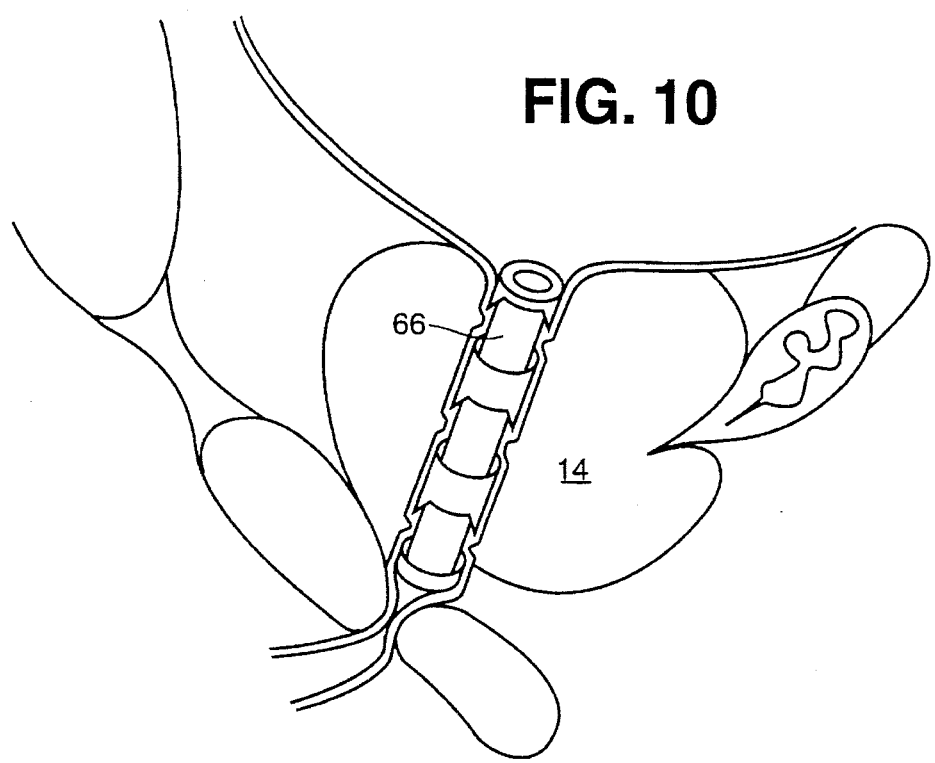
FIG. 10 is a perspective view of a further embodiment of this invention depicting an unexpanded stent having a notched anchoring configuration.

FIG. 10 represents a further embodiment of this invention. Grooves or notches 66 enable the expandable stent to be anchored in the desired position. A biocompatible adhesive present on the outside of the device of this invention, or adapted to be emitted from the device could also be employed for anchoring the device in the urethra, as desired.

Figure 11:
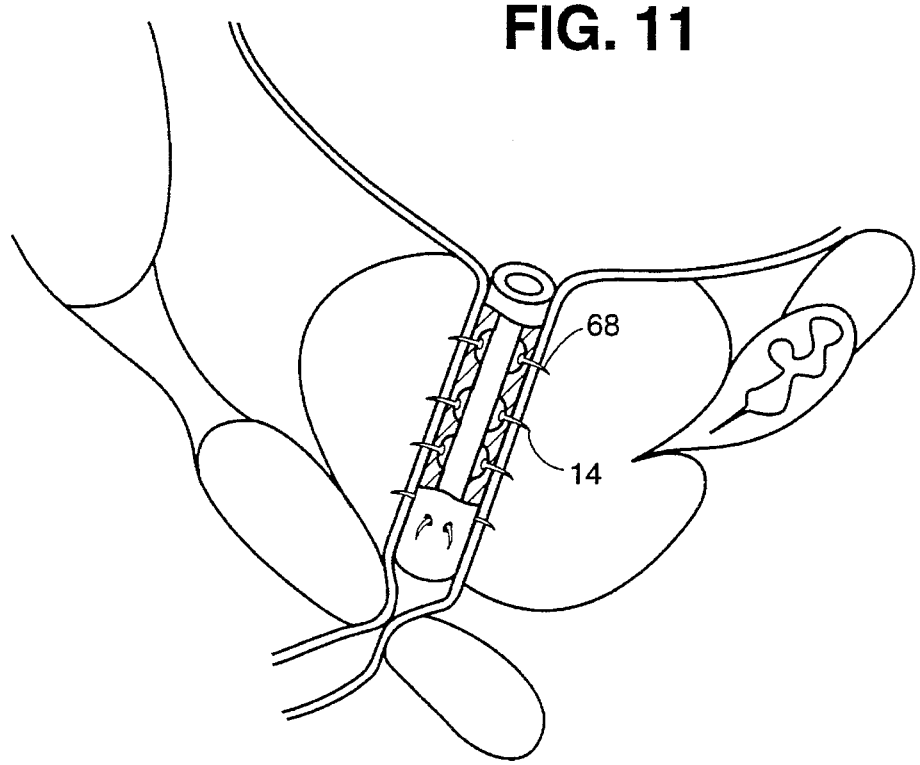
FIG. 11 is a perspective view of a further embodiment of this invention showing a stent having a spiked anchoring configuration.

Retractable "spikes" 68 can also be utilized to anchor the device in its intended position as shown in FIG. 11. These spikes would interstitially invest the prostate gland and fasten the device in the obstructed portion of the urethra. The spikes could be of a material which would dissolve after the passage of urine, or the spikes would be retractable by mechanical means. This can be accomplished by using a transurethral tool which would capture a portion of the spike or hook and draw such out of the tissue back into the urethral tool.

As shown in FIG. 9, the function of wire portion 58, in its coiled state, is to anchor the collapsible bag embodiment of this invention, and is another illustration of suitable anchoring means.

To operate the dilation device of this invention, employing the envelope embodiment for illustration, the first step is to insert the device into the urethra. The manner of doing so is not narrowly critical and means presently available can be utilized for this purpose.

After the envelope is positioned contiguous to the obstructed portion of the urethra, the hydrophilic means contained therein will begin to slowly expand due to the passage of water into the recesses of the envelope. The expansion will occur outwardly and radially since the outer surface is distensible while the inner core is not. As stated the expansion should occur gradually over a period of at least 30 minutes and preferably over a much longer period. The force of the expansion, as explained previously, is often self-limiting, when equilibrium is reached. This is usually after an expansion of from 100 to 1000 percent from the original diameter. The reacting pressure from the hypertrophied prostate gland, and/or the predetermined distensibility of the material of the outer surface of the envelope all aid in defining the extent of expansion and hence dilation to a desired maximum external diameter and configuration. Suitable anchoring means then fix the device in place. After a period of about 5 to about 30 days the device is removed.

For reasons which are not completely known, when the device of this invention is removed, the dilated urethra will tend to remain in its dilated configuration for a period on the order of about 12 to about 24 months, or longer, i.e. the patency of the urethral lumen or canal will tend to remain in its dilated state. It is believed that the slow dilation causes pressure necrosis of the tissue with fibrous collagen deposition within the parenchyma of the prostate. The fibrous tissue is not physiologically active thus reducing the ability of the prostate to contract. This scarring of the gland is much like that which occurs in the myocardium after infarction.

While this invention has particular applicability to the dilation of the prostatic urethra, another application would be to the slow dilation of the urethral stricture often encountered after multiple cystoscopic examination, such as for example in the area of the bulbous urethra.

It is apparent that other modifications and variations besides those specifically mentioned herein may be made in the devices described herein and depicted in the accompanying drawings without departing from the concept of the present invention.

We claim:

1. A dilation device for opening a portion of an obstructed urethra, which comprises, an inner hollow tubular core defining a lumen therewithin, said lumen being a conduit of sufficient diameter to permit urine to flow freely therethrough from the bladder, said core being substantially non-collapsible and containing access means enabling body fluids to pass through said core in a radially outwardly direction;

an outer confining covering capable of expanding radially outwardly to a predetermined extent, said covering having a length, disposed on said core, of at least partially that of the obstructed portion of the urethra; and hydrophilic material defined between said outer covering and said core capable of absorbing water and thereupon gradually swelling for a period of at least about 30 minutes, thereby to cause the outer covering to gradually expand radially outwardly until dilation of the obstructed portion of the urethra occurs to a desired diameter and configuration.

2. A dilation device according to claim 1, whereby said device is adapted to remain in the urethra with the hydrophilic means expanded, for a time sufficient that the dilated configuration of the urethra will tend to remain as such upon removal of the device, the inner core being non-collapsible under pressures that would emanate from a hypertrophied prostate gland and under the internal pressures exerted by the expanded hydrophilic material.

3. A dilation device according to claim 2, wherein the dilation device, in an undilated state, has a diameter of between about 20 and about 26 French.

4. A dilation device according to claim 1, wherein the hydrophilic material is capable of gradually swelling, at a rate of about 6 to about 10 French per 24 hour period, the upper limit of said expansion being self-limiting.

5. A dilation device according to claim 1, wherein the gradually expanding hydrophilic means is a cross-linked polymeric material which is insoluble but capable of absorbing water.

6. A dilation device according to claim 2, wherein said device is adapted to remain in the dilated portion of the urethra for a period of from about 5 days to about 30 days, and then removed from the urethra.

7. A dilation device according to claim 6, which additionally includes anchoring or fixing means which will retain the device within the urethra for the time desired without slippage or spontaneous movement therefrom.

8. A dilation device for opening a portion of a urethra obstructed as a consequence of a hypertrophied prostate gland, which comprises, an inner hollow tubular core defining a lumen therewithin, said lumen being a conduit of sufficient diameter to permit urine to flow freely therethrough from the bladder, said core being non-collapsible under pressures that would emanate from the hypertrophied prostate gland and containing access means enabling body fluids to pass through said core in a radially outwardly direction;

an outer confining covering in the form of an envelope disposed about at least a portion of said inner core, said envelope having an outer surface capable of expanding radially outwardly to a predetermined maximum diameter, said envelope having a length, disposed on said core, of at least partially that of the obstructed portion of the urethra; and hydrophilic material defined between said envelope and said core capable of absorbing water and thereupon gradually swelling for a period of at least about 30 minutes, thereby to cause the outer surface of the envelope to gradually expand radially outwardly and impact upon the prostate gland, until dilation of the obstructed portion of the urethra occurs to a desired diameter and configuration.

9. A dilation device according to claim 8, wherein the access means are a series of perforations having cross-sections smaller than the diameters of the hydrophilic material.

10. A dilation device according to claim 8, wherein the inner core comprises a permeable membrane.

11. A dilation device according to claim 8, wherein the device is adapted to remain in the urethra for a time sufficient that the dilated configuration of the urethra will tend to remain as such after removal of the device.

12. A dilation device according to claim 11, which includes means for removing said device from the urethra after a period of between about 5 and about 30 days.

13. A dilation device according to claim 12, which additionally includes anchoring or fixing means which will retain the device within the urethra for the time desired without slippage or spontaneous movement therefrom.

14. A dilation device according to claim 13, wherein the outer surface of the envelope expands at a rate of between 6 to 10 French per 24 hour period, the upper limit of such expansion being self-limiting.

15. A dilation device for opening a portion of a urethra obstructed as a consequence of a hypertrophied prostate gland, which comprises, an inner hollow tubular core defining a lumen therewithin, said lumen being a conduit of sufficient diameter to permit urine to flow freely therethrough from the bladder, said core being non-collapsible under pressures that would emanate from the hypertrophied prostate gland and containing access means enabling body fluids to pass through said core in a radially outwardly direction;

an outer confining covering in the form of a collapsible and expandable bag disposed about at least a portion of said core, said bag having on outer elastic surface capable of expanding radially outwardly, said bag having a length, disposed on said core, of at least partially that of the obstructed portion of the urethra; and hydrophilic material defined between said outer surface of said bag and said core capable of absorbing water and thereupon gradually swelling for a period of at least about 30 minutes, thereby to cause the outer surface of the bag to gradually expand radially outwardly until equilibrium is obtained between the radial pressures of the expanded hydrophilic material and the prostatic tissue, and until dilation of the obstructed portion of the urethra occurs to a desired diameter and configuration.

16. A dilation device according to claim 15, wherein the device is adapted to remain in the urethra for a time sufficient that the dilated configuration of the urethra will tend to remain as such after removal of the device.

17. A dilation device according to claim 16, which includes means for removing said device from the urethra after a period of between about 5 and about 30 days.

18. A dilation device according to claim 17, which additionally includes anchoring or fixing means which will retain the device within the urethra for the time desired without slippage or spontaneous movement therefrom.

19. A dilation device according to claim 18, wherein the outer surface of the bag expands at a rate of between 6 and 10 French per 24 hour period.

20. A dilation device according to claim 18, wherein said anchoring or fixing means comprise a filament attached at one end to said core and traversing through at least a portion of said core, said filament further extending out of said core and having a portion thereof capable of being reversibly coiled or straightened when positioned in the area of the external sphincter, which when in a coiled mode will provide an anchoring or fixing mechanism for the device.

21. A dilation device according to claim 15 whereby to effect removal thereof, the collapsible bag is initially torn and collapsed by externally applied means.

22. A method of dilating a portion of a urethra obstructed as a consequence of a hypertrophied prostate gland, by inserting a device into the urethra comprising, an inner hollow tubular core defining a lumen therewithin, said lumen being a conduit of sufficient diameter to permit urine to flow freely therethrough from the bladder, said core being non-collapsible under pressures that would emanate from the hypertrophied prostate gland and containing access means enabling body fluids to pass through said core in a radially outwardly direction; and having an outer confining covering capable of expanding radially outwardly to a predetermined extent, said covering having a length, disposed on said core, of at least partially that of the obstructed portion of the urethra; and having hydrophilic material defined between said outer covering and said core capable of absorbing water and thereupon gradually swelling for a period of at least about 30 minutes;

disposing the device within at least the length of the obstructed portion; and leaving said device within the urethra for at least 30 minutes until the hydrophilic means swell due to the uptake of body fluids, whereby the outer covering expands to the extent dilation of the obstructed portion of the urethra occurs to a desired diameter and configuration.

23. A method according to claim 22, wherein the device remains in the urethra for a time sufficient so that the dilated configuration will tend to remain in such configuration after the device is removed.

24. A method according to claim 22 wherein the hydrophilic means expands at a rate of between 6 and 10 French per 24 hour period, the expansion being self-limiting.

25. A method according to claim 23, Wherein the device remains in the urethra for a period of from about 5 days to about 30 days before being removed from the urethra.

26. A method according to claim 22, wherein the outer confining covering is in the form of an envelope having an outer surface capable of expanding to a predetermined diameter.

27. A method according to claim 22, wherein the outer confining covering is in a form of a collapsible and expandable bag, having an elastic outer surface capable of expanding to the extent where equilibrium is obtained between the radial pressures of the expanded hydrophilic material and the prostatic tissue.

28. A method of treating benign prostatic hyperplasia which comprises, inserting a dilation device into a urethra obstructed as a consequence of the prostatic hyperplasia, said device having hydrophilic means integrally associated therewith which are adapted to gradually swell and then expand radially outwardly when water is absorbed by said means, retaining said device within at least the obstructed portion of the urethra for a period of at least about 30 minutes whereby the hydrophilic means swell due to the uptake of body fluids and gradually expand radially and outwardly to effect a desired dilation of the obstructed portion, leaving the device in the urethra for a period of between about 5 and about 30 days, and removing the device from the urethra, the dilated portion of the urethra thereby tending to remain in such dilated configuration.

* * * * *